United States Patent
Ruhland et al.

(10) Patent No.: US 8,110,567 B2
(45) Date of Patent: Feb. 7, 2012

(54) PHENYL-PIPERAZINE DERIVATIVES AS SEROTONIN REUPTAKE INHIBITORS

(75) Inventors: Thomas Ruhland, Roskilde (DK); Garrick Paul Smith, Valby (DK); Benny Bang-Andersen, Copenhagen (DK); Ejner Knud Moltzen, Gentofte (DK); Kim Andersen, Ridgewood, NJ (US); Ask Puschl, Frederiksberg (DE)

(73) Assignee: H. Lundbeck A/S, Valby-Copenhagen (DK)

( * ) Notice: Subject to any disclaimer, the term of this patent is extended or adjusted under 35 U.S.C. 154(b) by 0 days.

(21) Appl. No.: 12/700,521

(22) Filed: Feb. 4, 2010

(65) Prior Publication Data

US 2011/0009423 A1 Jan. 13, 2011

Related U.S. Application Data

(60) Division of application No. 11/551,188, filed on Oct. 19, 2006, now Pat. No. 7,683,053, which is a continuation of application No. 10/488,280, filed as application No. PCT/DK02/00659 on Oct. 2, 2002, now Pat. No. 7,144,884.

(30) Foreign Application Priority Data

Oct. 4, 2001 (DK) .................................. 2001 01466

(51) Int. Cl.
*A61P 25/22* (2006.01)
*A61K 31/55* (2006.01)
*C07D 403/00* (2006.01)
*C07D 243/00* (2006.01)

(52) U.S. Cl. .............. 514/212.01; 514/212.02; 540/543; 540/603

(58) Field of Classification Search ............ 514/212.01, 514/212.02; 540/543, 603
See application file for complete search history.

(56) References Cited

U.S. PATENT DOCUMENTS

| 4,198,417 A | 4/1980 | Ong et al. |
| 4,198,419 A | 4/1980 | Ong et al. |
| 4,241,071 A | 12/1980 | Martin et al. |
| 4,859,675 A | 8/1989 | Foguet et al. |

FOREIGN PATENT DOCUMENTS

| EP | 0301549 A1 | 2/1989 |
| EP | 0 755 923 A1 | 1/1997 |
| GB | 1 489 711 | 10/1977 |
| WO | 9917777 A1 | 4/1999 |
| WO | 00/59878 A2 | 10/2000 |
| WO | 01/10842 A2 | 2/2001 |
| WO | 01/49678 A1 | 7/2001 |
| WO | 01/49681 A1 | 7/2001 |
| WO | 02/059108 A1 | 8/2002 |
| WO | 02/062766 A2 | 8/2002 |
| WO | 2004/085385 A2 | 10/2004 |
| WO | 2005/000309 A2 | 1/2005 |

OTHER PUBLICATIONS

Lawrence L. Martin, et al. "Synthesis of Spiro[isobenzofur4an-1(3 H), 4'-piperidines] as Potential Central Nervous System Agents. 5. Conformationally Mobile Analogues Derived by Furan Ring Opening", Journal of Medicinal Chemistry, 1979, vol. 22, No. 11, pp. 1347-1354.
Ruhland et al. Chemical Abstract, vol. 135, No. 107345, Abstract for WO 2001/049678, 2001.
Medicinal Chemistry (2nd Ed.) edited by Alfred Burger, pp. 72-78 (1960).

*Primary Examiner* — Brenda Coleman
(74) *Attorney, Agent, or Firm* — Fish & Richardson P.C.

(57) ABSTRACT

The invention provides compounds represented by the general formula I

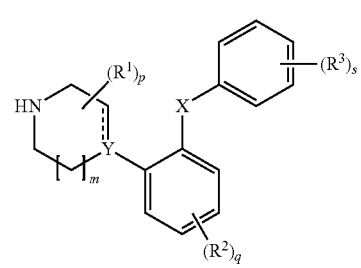

wherein the substituents are defined in the application. The compounds are useful in the treatment of an affective disorder, including depression, anxiety disorders including general anxiety disorder and panic disorder and obsessive compulsive disorder.

12 Claims, No Drawings

PHENYL-PIPERAZINE DERIVATIVES AS SEROTONIN REUPTAKE INHIBITORS

CROSS REFERENCES TO RELATED APPLICATIONS

This application is a divisional of U.S. patent application Ser. No. 11/551,188, filed Oct. 19, 2006, now U.S. Pat. No. 7,683,053, which is a continuation of Ser. No. 10/488,280, filed Jun. 15, 2004, which is now U.S. Pat. No. 7,144,884, which is a 371 National Stage of International Application No. PCT/DK2002/000659, filed Oct. 2, 2002, and which claims priority of Danish Application No. PA 2001 01466, filed Oct. 4, 2001. Each of the foregoing applications and patents is hereby incorporated by reference in its entirety.

The present invention relates to novel compounds which are serotonin reuptake inhibitors and as such effective in the treatment of for example depression and anxiety.

BACKGROUND OF THE INVENTION

Selective serotonin reuptake inhibitors (hereinafter referred to as SSRIs) have become first choice therapeutics in the treatment of depression, certain forms of anxiety and social phobias, because they are effective, well tolerated and have a favourable safety profile compared to the classic tricyclic antidepressants.

However, clinical studies on depression indicate that non-response to SSRIs is substantial, up to 30%. Another, often neglected, factor in antidepressant treatment is compliance, which has a rather profound effect on the patient's motivation to continue pharmacotherapy.

First of all, there is the delay in therapeutic effect of SSRIs. Sometimes symptoms even worsen during the first weeks of treatment. Secondly, sexual dysfunction is a side effect common to all SSRIs. Without addressing these problems, real progress in the pharmacotherapy of depression and anxiety disorders is not likely to happen.

In order to cope with non-response, psychiatrists sometimes make use of augmentation strategies. Augmentation of antidepressant therapy may be accomplished through the co-administration of mood stabilizers such as lithium carbonate or triiodothyronin or by the use of electroshock.

The effect of combined administration of a compound that inhibits serotonin reuptake and a $5\text{-HT}_{1A}$ receptor antagonist has been evaluated in several studies (Innis et al. *Eur. J. Pharmacol.* 1987, 143, 1095-204 and Gartside *Br. J. Pharmacol.* 1995, 115, 1064-1070, Blier et al. *Trends in Pharmacol. Science* 1994, 15, 220). In these studies, it was found that $5\text{-HT}_{1A}$ receptor antagonists would abolish the initial brake on 5-HT neurotransmission induced by the serotonin reuptake inhibitors and thus produce an immediate boost of 5-HT transmission and a rapid onset of therapeutic action.

Several patent applications have been filed, which cover the use of a combination of a $5\text{-HT}_{1A}$ antagonist and a serotonin reuptake inhibitor for the treatment of depression (see e.g. EP-A2-687472 and EP-A2-714663).

Another approach to increase terminal 5-HT would be through blockade of the $5\text{-HT}_{1B}$ autoreceptor. Microdialysis experiments in rats have indeed shown that increase of hippocampal 5-HT by citalopram is potentiated by GMC 2-29, an experimental $5\text{-HT}_{1B}$ receptor antagonist.

Several patent applications covering the combination of an SSRI and a $5\text{-HT}_{1B}$ antagonist or partial agonist have also been filed (WO 97/28141, WO 96/03400, EP-A-701819 and WO 99/13877).

It has previously been found that the combination of a serotonin reuptake inhibitor with a compound having $5\text{-HT}_{2C}$ antagonistic or inverse agonistic effect (compounds having a negative efficacy at the $5\text{-HT}_{2C}$ receptor) provides a considerable increase in the level of 5-HT in terminal areas, as measured in microdialysis experiments (WO 01/41701). This would imply a shorter onset of antidepressant effect in the clinic and an augmentation or potentiation of the therapeutic effect of the serotonin reuptake inhibitor (SRI).

The present invention provides compounds which are serotonin reuptake inhibitors for the treatment of affective disorders such as depression, anxiety disorders including general anxiety disorder and panic disorder and obsessive compulsive disorder. Some of the compounds also have a combined effect of serotonin reuptake inhibition and $5\text{-HT}_{2C}$ receptor modulation, which according to WO01/41701 would imply a faster onset of anti-depressant activity.

A few of the compounds embraced by the present invention have previously been described in WO 01/49681 and in WO02/59108 However, the compounds of WO01/49681 are not disclosed as having any therapeutic or biological activity. The compounds of WO02/59108 are disclosed as intermediates in the synthesis of compounds different from the compounds of the present invention with a therapeutic activity as melanocortin receptor agonists. One compound, 1-(2-phenoxyphenyl)-piperazine, embraced by the present invention, is disclosed in U.S. Pat. No. 4,064,245 as being useful in the treatment of metabolic disorders.

SUMMARY OF THE INVENTION

The present invention provides compounds of the general formula I

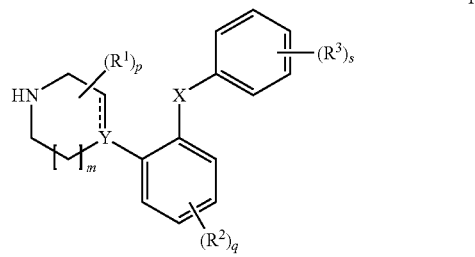

wherein
Y is N, C or CH;
X represent O or S;
m is 1 or 2;
p is 0, 1, 2, 3, 4, 5, 6, 7 or 8;
q is 0, 1, 2, 3 or 4;
s is 0, 1, 2, 3, 4 or 5;
The dotted line represents an optional bond;
Each $R^1$ is independently selected from the group represented by $C_{1-6}$-alkyl, or two $R^1$ attached to the same carbon atom may form a 3-6-membered spiro-attached cyclo-alkyl;
Each $R^2$ is independently selected from the groups represented by halogen, cyano, nitro, $C_{1-6}$-alk(en/yn)yl, $C_{1-6}$-alk(en/yn)yloxy, $C_{1-6}$-alk(en/yn)ylsulfanyl, hydroxy, hydroxy-$C_{1-6}$-alk(en/yn)yl, halo-$C_{1-6}$-alk(en/yn)yl, halo-$C_{1-6}$-alk(en/yn)yloxy, $C_{3-8}$-cycloalk(en)yl, $C_{3-8}$-cycloalk(en)yl-$C_{1-6}$-alk(en/yn)yl, acyl, $C_{1-6}$-alk(en/yn)yloxycarbonyl, $C_{1-6}$-alk(en/yn)ylsulfonyl, or —$NR^xR^y$;
Each $R^3$ is independently selected from a group represented by halogen, cyano, nitro, $C_{1-6}$-alk(en/yn)yl, $C_{1-6}$-alk(en/yn)

yloxy, $C_{1-6}$-alk(en/yn)ylsulfanyl, hydroxy, hydroxy-$C_{1-6}$-alk(en/yn)yl, halo-$C_{1-6}$-alk(en/yn)yl, halo-$C_{1-6}$-alk(en/yn)yloxy, $C_{3-8}$-cycloalk(en)yl, $C_{3-8}$-cycloalk(en)yl-$C_{1-6}$-alk(en/yn)yl, $C_{1-6}$-alk(en/yn)ylsulfonyl, aryl, $C_{1-6}$-alk(en/yn)yloxycarbonyl, acyl, —NR$^x$CO—$C_{1-6}$-alk(en/yn)yl, CONR$^x$R$^y$ or NR$^x$R$^y$;

or two adjacent R$^3$ substituents together form a heterocycle fused to the phenyl ring selected from the group consisting of

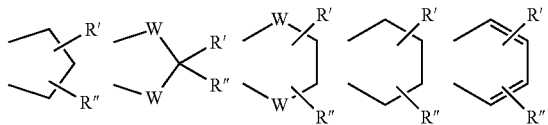

wherein W is O or S, and R' and R" are hydrogen or $C_{1-6}$-alkyl:

or two adjacent R$^3$ substituents together form a fused heteroaromatic system containing one, two or three heteroatoms, wherein each R$^x$ and R$^y$ is independently selected from the group represented by hydrogen, $C_{1-6}$-alk(en/yn)yl, $C_{3-8}$-cycloalk(en)yl, $C_{3-8}$-cycloalk(en)yl-$C_{1-6}$alk(en/yn)yl, or aryl; or R$^x$ and R$^y$ together with the nitrogen to which they are attached form a 3-7-membered ring which optionally contains one further heteroatom;

or an acid addition salt thereof.

The invention also provides compounds as above provided that the compound is not 1-(2-phenoxyphenyl)-piperazine;

The invention also provides compounds as above provided that the compound is not 1-[2-(2-Methoxyphenoxy)phenyl]piperazine, 1-[2-(2,6-dimethoxyphenoxy)phenyl][1,4]-diazepane, 1-{2-[3-(dimethylamino)phenoxy]phenyl}piperazine, 1-[2-(4-methylphenoxy)phenyl]piperazine, 1-[2-(3-methylphenoxy)phenyl]piperazine, 1-[2-(3-chlorophenoxy)phenyl]piperazine, 1-[2-(3-methoxyphenoxy)phenyl]piperazine and 1-(2-phenoxyphenyl)-piperazine;

The invention provides a compound according to the above for use as a medicament.

The invention provides a pharmaceutical composition comprising a compound according to the above or a pharmaceutically acceptable acid addition salt thereof and at least one pharmaceutically acceptable carrier or diluent.

The invention provides the use of a compound according to the above or a pharmaceutically acceptable acid addition salt thereof for the preparation of a medicament for the treatment of affective disorders, such as depression, anxiety disorders including general anxiety disorder and panic disorder and obsessive compulsive disorder.

The invention provides a method for the treatment of an affective disorder, including depression, anxiety disorders including general anxiety disorder and panic disorder and obsessive compulsive disorder in a living animal body, including a human, comprising administering a therapeutically effective amount of a compound according to the above or a pharmaceutically acceptable acid addition salt thereof.

DETAILED DESCRIPTION OF THE INVENTION

Preferred embodiments of the invention are wherein p is 0;
Preferred embodiments of the invention are wherein m is 1 or 2;
Preferred embodiments of the invention are R$^2$ is trifluoromethyl, or $C_{1-6}$-alkyl;

Preferred embodiments of the invention are wherein R$^3$ is selected from the group consisting of halogen, $C_{1-6}$-alkoxy, $C_{1-6}$-sulfanyl, $C_{1-6}$-alkyl, hydroxy or trifluoromethyl;

Particularly preferred embodiments of the invention are wherein the compound of the invention is any of the following:

1-[2-(2-Trifluoromethylphenylsulfanyl)phenyl]piperazine,
1-[2-(4-Bromophenylsulfanyl)phenyl]piperazine,
1-{2-[4-(Methylsulfanyl)phenylsulfanyl]phenyl}piperazine,
1-[2-(4-Hydroxyphenylsulfanyl]phenyl}piperazine,
1-[2-(2,4-Dimethylphenylsulfanyl)phenyl]piperazine,
1-[2-(3,5-Dimethylphenylsulfanyl)phenyl]piperazine,
1-[2-(2,6-Dimethylphenylsulfanyl)phenyl]piperazine,
1-[2-(2,5-Dimethylphenylsulfanyl)phenyl]piperazine,
1-[2-(2-Trifluoromethylphenylsulfanyl)phenyl][1,4]-diazepane,
1-[2-(3-Methylphenylsulfanyl)phenyl][1,4]-diazepane,
1-[2-(4-Butylphenoxy)phenyl]piperazine,
1-[2-(4-Methoxyphenoxy)phenyl]piperazine,
2-(4-Methylphenylsulfanyl)phenyl-1-piperazine,
1-[2-(4-Chlorophenylsulfanyl)phenyl]-piperazine,
1-[2-(4-Methoxyphenylsulfanyl)-4-chlorophenyl]piperazine,
1-[2-(4-Methoxyphenylsulfanyl)-4-methylphenyl]piperazine,
1-[2-(4-Methoxyphenylsulfanyl)-5-methylphenyl]piperazine,
1-[2-(4-Fluorophenylsulfanyl)-5-methylphenyl]piperazine,
1-[2-(4-Methoxyphenylsulfanyl)-5-trifluoromethylphenyl]piperazine,
1-[2-(4-Chlorophenylsulfanyl)phenyl]-3-methylpiperazine,
1-[2-(4-Chlorophenylsulfanyl)phenyl]-3,5-dimethylpiperazine,
4-[2-(4-Methylphenylsulfanyl)phenyl]-3,6-dihydro-2H-pyridine,
4-[2-(4-Methoxyphenylsulfanyl)phenyl]-3,6-dihydro-2H-pyridine or
4-[2-(4-Methylphenylsulfanyl)phenyl]piperidine or a pharmaceutically acceptable acid addition salt thereof.

Definition of Substituents

Halogen means fluoro, chloro, bromo or iodo.

The expression $C_{1-6}$-alk(en/Yn)yl means a $C_{1-6}$-alkyl, $C_{2-6}$-alkenyl or a $C_{2-6}$-alkynyl group. The expression $C_{3-8}$-cycloalk(en)yl means a $C_{3-8}$-cycloalkyl- or cycloalkenyl group.

The term $C_{1-6}$ alkyl refers to a branched or unbranched alkyl group having from one to six carbon atoms inclusive, including but not limited to methyl, ethyl, 1-propyl, 2-propyl, 1-butyl, 2-butyl, 2-methyl-2-propyl and 2-methyl-1-propyl.

Similarly, $C_{2-6}$ alkenyl and $C_{2-6}$ alkynyl, respectively, designate such groups having from two to six carbon atoms, including one double bond and one triple bond respectively, including but not limited to ethenyl, propenyl, butenyl, ethynyl, propynyl and butynyl.

The term $C_{3-8}$ cycloalkyl designates a monocyclic or bicyclic carbocycle having three to eight C-atoms, including but not limited to cyclopropyl, cyclopentyl, cyclohexyl, etc.

The term $C_{3-8}$ cycloalkenyl designates a monocyclic or bicyclic carbocycle having three to eight C-atoms and including one double bond.

In the term $C_{3-8}$-cycloalk(en)yl-$C_{1-6}$-alk(en/yn)yl, $C_{3-8}$-cycloalk(en)yl and $C_{1-6}$-alk(en/yn)yl are as defined above.

The terms $C_{1-6}$-alk(en/yn)yloxy, $C_{1-6}$ alk(en/yn)ylsulfanyl, hydroxy-$C_{1-6}$-alk(en/yn)yl, halo-$C_{1-6}$-alk(en/yn)yl, halo-$C_{1-6}$-alk(en/yn)yloxy, $C_{1-6}$-alk(en/yn)ylsulfonyl etc. designate such groups in which the $C_{1-6}$-alk(en/yn)yl are as defined above.

As used herein, the term $C_{1-6}$-alk(en/yn)yloxycarbonyl refers to groups of the formula $C_{1-6}$-alk(en/yn)yl—O—CO—, wherein $C_{1-6}$-alk(en/yn)yl are as defined above.

As used herein, the term acyl refers to formyl, $C_{1-6}$-alk(en/yn)ylcarbonyl, arylcarbonyl, aryl-$C_{1-6}$-alk(en/yn)ylcarbonyl, $C_{3-8}$-cycloalk(en)ylcarbonyl or a $C_{3-8}$-cycloalk (en)yl-$C_{1-6}$-alk(en/yn)yl-carbonyl group.

The term 3-7-membered ring optionally containing one further heteroatom as used herein refers to ring systems such as 1-morpholinyl, 1-piperidinyl, 1-azepinyl, 1-piperazinyl, 1-homopiperazinyl, 1-imidazolyl, 1-pyrrolyl or pyrazolyl, all of which may be further substituted with $C_{1-6}$-alkyl.

The heterocycles formed by two adjacent $R^3$ substituents and fused to the parent ring may together form rings such as 5-membered monocyclic rings such as 3H-1,2,3-oxathiazole, 1,3,2-oxathiazole, 1,3,2-dioxazole, 3H-1,2,3-dithiazole, 1,3,2-dithiazole, 1,2,3-oxadiazole, 1,2,3-thiadiazole, 1H-1,2,3-triazole, isoxazole, oxazole, isothiazole, thiazole, 1H-imidazole, 1H-pyrazole, 1H-pyrrole, furan or thiophene and 6-membered monocyclic rings such as 1,2,3-oxathiazine, 1,2,4-oxathiazine, 1,2,5-oxathiazine, 1,4,2-oxathiazine, 1,4,3-oxathiazine, 1,2,3-dioxazine, 1,2,4-dioxazine, 4H-1,3,2-dioxazine, 1,4,2-dioxazine, 2H-1,5,2-dioxazine, 1,2,3-dithiazine, 1,2,4-dithiazine, 4H-1,3,2-dithiazine, 1,4,2-dithiazine, 2H-1,5,2-dithiazine, 2H-1,2,3-oxadiazine, 2H-1,2,4-oxadiazine, 2H-1,2,5-oxadiazine, 2H-1,2,6-oxadiazine, 2H-1,3,4-oxadiazine, 2H-1,2,3-thiadiazine, 2H-1,2,4-thiadiazine, 2H-1,2,5-thiadiazine, 2H-1,2,6-thiadiazine, 2H-1,3,4-thiadiazine, 1,2,3-triazine, 1,2,4-triazine, 2H-1,2-oxazine, 2H-1,3-oxazine, 2H-1,4-oxazine, 2H-1,2-thiazine, 2H-1,3-thiazine, 2H-1,4-thiazin, pyrazine, pyridazine, pyrimidine, 4H-1,3-oxathiin, 1,4-oxathiin, 4H-1,3-dioxin, 1,4-dioxin, 4H-1,3-dithiin, 1,4-dithiin, pyridine, 2H-pyran or 2H-thiin.

The term aryl refers to carbocyclic, aromatic systems such as phenyl and naphtyl.

The acid addition salts of the invention are preferably pharmaceutically acceptable salts of the compounds of the invention formed with non-toxic acids. Exemplary of such organic salts are those with maleic, fumaric, benzoic, ascorbic, succinic, oxalic, bis-methylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, benzenesulfonic and theophylline acetic acids, as well as the 8-halotheophyllines, for example 8-bromotheophylline. Exemplary of such inorganic salts are those with hydrochloric, hydrobromic, sulfuric, sulfamic, phosphoric and nitric acids.

Further, the compounds of this invention may exist in unsolvated as well as in solvated forms with pharmaceutically acceptable solvents such as water, ethanol and the like. In general, the solvated forms are considered equivalent to the unsolvated forms for the purposes of this invention.

Some of the compounds of the present invention contain chiral centres and such compounds exist in the form of isomers (i.e. enantiomers). The invention includes all such isomers and any mixtures thereof including racemic mixtures.

Racemic forms can be resolved into the optical antipodes by known methods, for example, by separation of diastereomeric salts thereof with an optically active acid, and liberating the optically active amine compound by treatment with a base. Another method for resolving racemates into the optical antipodes is based upon chromatography on an optically active matrix. Racemic compounds of the present invention can also be resolved into their optical antipodes, e.g. by fractional crystallization of d- or l-(tartrates, mandelates or camphorsulphonate) salts. The compounds of the present invention may also be resolved by the formation of diastereomeric derivatives.

Additional methods for the resolution of optical isomers, known to those skilled in the art, may be used. Such methods include those discussed by J. Jaques, A. Collet and S. Wilen in "Enantiomers, Racemates, and Resolutions", John Wiley and Sons, New York (1981).

Optically active compounds can also be prepared from optically active starting materials.

Pharmaceutical Compositions

The pharmaceutical formulations of the invention may be prepared by conventional methods in the art. For example: Tablets may be prepared by mixing the active ingredient with ordinary adjuvants and/or diluents and subsequently compressing the mixture in a conventional tabletting machine. Examples of adjuvants or diluents comprise: corn starch, potato starch, talcum, magnesium stearate, gelatine, lactose, gums, and the like. Any other adjuvants or additives usually used for such purposes such as colourings, flavourings, preservatives etc. may be used provided that they are compatible with the active ingredients.

Solutions for injections may be prepared by dissolving the active ingredient and possible additives in a part of the solvent for injection, preferably sterile water, adjusting the solution to desired volume, sterilising the solution and filling it in suitable ampules or vials. Any suitable additive conventionally used in the art may be added, such as tonicity agents, preservatives, antioxidants, etc.

The pharmaceutical compositions of this invention or those which are manufactured in accordance with this invention may be administered by any suitable route, for example orally in the form of tablets, capsules, powders, syrups, etc., or parenterally in the form of solutions for injection. For preparing such compositions, methods well known in the art may be used, and any pharmaceutically acceptable carriers, diluents, excipients or other additives normally used in the art may be used.

Conveniently, the compounds of the invention are administered in unit dosage form containing said compounds in an amount of about 0.01 to 100 mg. The total daily dose is usually in the range of about 0.05-500 mg, and most preferably about 0.1 to 50 mg of the active compound of the invention.

The compounds of the invention are prepared by the following general methods:

a) Deprotection or Cleavage from a Polymer Support of a Compound with Formula II

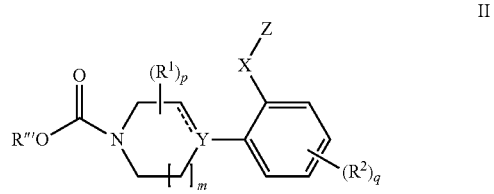

II wherein Z represents

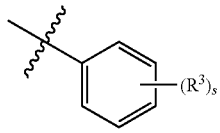

and $R^1$, $R^2$, $R^3$, m, p, q, s, X, Y and the dotted line are as described above, and R''' is a tert-butyl, methyl, ethyl, allyl or benzyl group or $R'''OCO_2$ is a solid supported carbamate group, such as the Wang resin-based carbamate linker.

b) Chemical Transformation of a Compound with Formula III

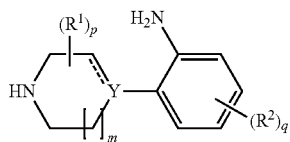

III wherein $R^1$, $R^2$, m, p, q, Y and the dotted line are as described above, to the corresponding diazonium compound, and subsequently reacting with a compound HXZ, wherein X and Z are as defined above.

c) Reacting a Compound with Formula IV

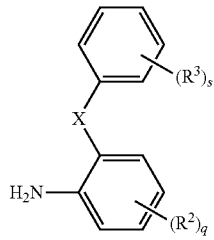

IV wherein $R^2$, $R^3$, X, s and q are as described above with an alkylating agent of formula $(Cl-(CH_2)_{m+1})NH(CH_2)_2Cl$ or $(Br-(CH_2)_{m+1})NH(CH_2)_2Br$ wherein m are as defined above.

d) Reacting a Compound with Formula V

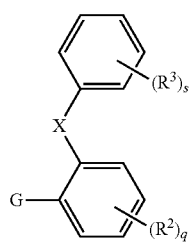

V wherein $R^2$, $R^3$, X, s and q are as described above and G is a bromine or iodine atom with a compound of formula VI

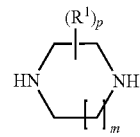

VI wherein $R^1$, m and p are as defined above.

e) Dehydrating and Optionally Simultaneously Deprotecting a Compound of Formula VII

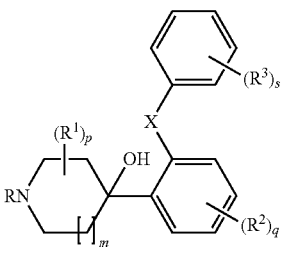

VII wherein $R^1$, $R^2$, $R^3$, X, m, p, q and s are as described above and R is either a hydrogen atom or a BOC group.

f) Hydrogenate the Double Bond in a Compound of Formula VIII

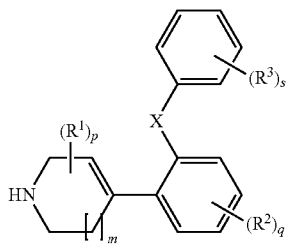

VIII wherein $R^1$, $R^2$, $R^3$, X, m, p, q and s are as described above.

The deprotection according to method a) was performed by standard techniques, known to the persons skilled in the art and detailed in the textbook *Protective Groups in Organic Synthesis* T. W. Greene and P. G. M. Wuts, Wiley Interscience, (1991) ISBN 0471623016.

Starting materials of formula II wherein R'''=tert-Bu were prepared according to the procedure as outlined below. Fluoronitrobenzene derivatives were reacted with phenols or thiophenols according to the procedure of Sawyer et al. *J. Org. Chem.* 1998, 63, 6338 followed by reduction using standard procedures known to the persons skilled in the art. This includes reduction to the corresponding aniline using a metal hydride salt such as sodium borohydride in conjunction with palladium on carbon catalyst in an alcoholic solvent or reduction using a metal chloride salt such as zinc chloride or tin chloride. The resulting aniline was then converted to a properly substituted 3,5-diketopiperazine in a modification of the procedure of Kruse et al. *Recl. Trav. Chim. Pays-Bas* 1998, 107, 303 using N-butyloxycarbonyliminodiacetic acid. The 3,5-diketopiperazine derivative was then reduced with for example borane to the corresponding BOC protected piperazine, which was then deprotected to the piperazine in situ.

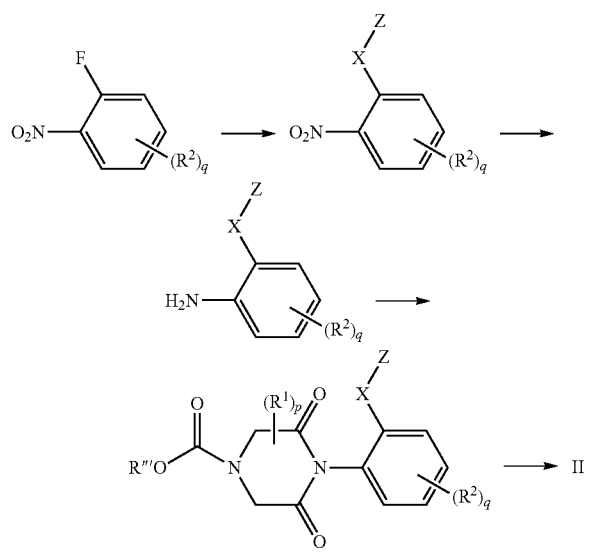

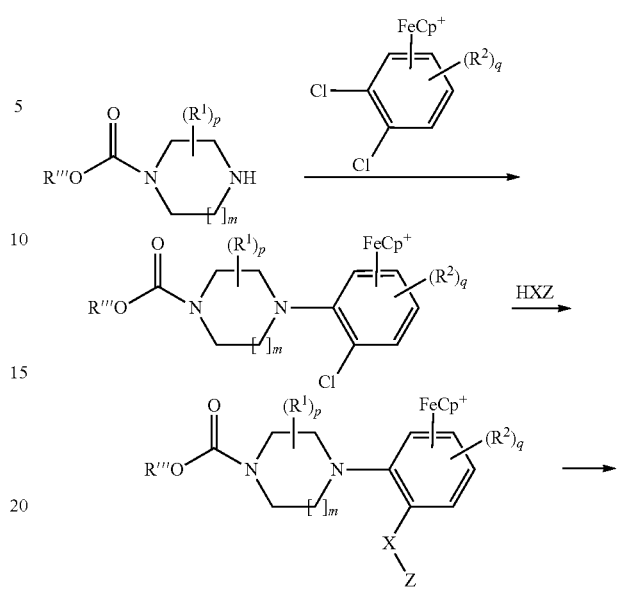

II

The compounds shown in formula II, wherein Y=CH and the optional double bond is reduced, were prepared from their tertiary alcohol precursors VII wherein R is a BOC group, by a modified Barton reduction in a similar manner as described in Hansen et al. *Synthesis* 1999, 1925-1930. The intermediate tertiary alcohols were prepared from the corresponding properly substituted 1-bromo-phenylsulfanylbenzenes or their corresponding ethers by metal-halogen exchange followed by addition of an appropriate electrophile of the formula IX in a similar manner as described in Palmer et al. *J. Med. Chem.* 1997, 40, 1982-1989. The properly substituted 1-bromo-phenylsulfanylbenzenes were prepared in a similar manner as described in the literature by reaction of properly substituted thiophenols with properly substituted aryliodides according to Schopfer and Schlapbach *Tetrahedron* 2001, 57, 3069-3073 Bates et al., *Org. Lett.* 2002, 4, 2803-2806 and Kwong et al. *Org. Lett.* 2002, 4, (in press). The corresponding substituted 1-bromo-phenoxybenzenes may be prepared as described by Buck et al. *Org. Lett.* 2002, 4, 1623-1626.

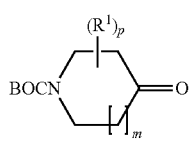

IX

The cleavage from a polymer support, such as from the Wang resin based carbamate linker, according to method a) was performed according to literature known procedures (Zaragoza *Tetrahedron Lett.* 1995, 36, 8677-8678 and Conti et al. *Tetrahedron Lett.* 1997, 38, 2915-2918).

The starting material of formula II may also be prepared according to the methods described in patent application WO 01/49681. The diamines were either commercially available or synthesised by methods known to chemists skilled in the art. Iron-complexes, like $\eta^6$-1,2-dichlorobenzene-$\eta^5$-cyclopentadienyliron(II) hexafluorophosphate and substituted analogues were synthesised according to literature known procedures (Pearson et al. *J. Org. Chem.* 1996, 61, 1297-1305) or synthesised by methods known to chemists skilled in the art.

The diazotation followed by reaction with a compound HXZ according to the method b) was performed by addition of the diazonium salt of the corresponding aniline to a solution of sodium salt of a thiophenol or a phenol in an aqueous suspension of copper. The starting material of formula III was prepared as outlined in the following. A fluoronitrobenzene derivative was reacted with a piperazine derivative in a solvent such as DMF, NMP or other dipolar aprotic solvent containing an organic base such as triethylamine to afford the orthonitophenylpiperazine derivative. The intermediate orthonitrophenylpiperazine was subsequently reduced using standard procedures as stated above to give the starting material of formula III.

The reaction of a compound of formula IV with an alkylating agent of formula (Cl—(CH$_2$)$_{m+1}$)NH(CH$_2$)$_2$Cl or (Br—(CH$_2$)$_{m+1}$)NH(CH$_2$)$_2$Br as its hydrobromide or hydrochloride salt, wherein m is as defined above was performed in a similar manner as described in Sircar et al. *J. Med. Chem.* 1992, 35, 4442-4449. Starting materials of formula IV were prepared as described above for starting materials of formula II.

The reaction of a compound of formula V with a diamine of formula VI in method d) was performed in a similar manner as described in Nishiyama et al. *Tetrahedron Lett.* 1998, 39, 617-620. The starting material of formula V was prepared in a similar manner as described in Schopfer et al. *Tetrahedron* 2001, 57, 3069-3073.

The dehydration reaction and optional simultaneous deprotection of a compound of formula VII in method e) was performed in a similar manner as described in Palmer et al *J. Med. Chem.* 1997, 40, 1982-1989. The starting material of formula VII wherein R=H was prepared from a compound of formula VII wherein R is a BOC group (see above) by deprotection with hydrochloric acid in methanol. Compounds of formula VII wherein R=BOC, may be prepared as described in Palmer et al. *J. Med. Chem.* 1997, 40, 1982-1989.

The reduction of the double bond according to method f) was generally performed by catalytic hydrogenation at low pressure (<3 atm.) in a Parr apparatus, or by using reducing agents such as diborane or hydroboric derivatives as produced in situ from NaBH$_4$ in trifluoroacetic acid in inert solvents such as tetrahydrofuran (THF), dioxane, or diethyl ether. The starting material of formula VIII was prepared from II as described in method a).

EXAMPLES

Analytical LC-MS data were obtained on a PE Sciex API 150EX instrument equipped with IonSpray source and Shimadzu LC-8A/SLC-10A LC system. Column: 30×4.6 mm Waters Symmmetry C18 column with 3.5 µm particle size; Solventsystem: A=water/trifluoroacetic acid (100:0.05) and B=water/acetonitrile/trifluoroacetic acid (5:95:0.03); Method: Linear gradient elution with 90% A to 100% B in 4 min and with a flow rate of 2 mL/min. Purity was determined by integration of the UV (254 nm) and ELSD trace. The retention times (RT) are expressed in minutes.

Preparative LC-MS-purification was performed on the same instrument. Column: 50×20 mm YMC ODS-A with 5 µm particle size; Method: Linear gradient elution with 80% A to 100% B in 7 min and with a flow rate of 22.7 mL/min. Fraction collection was performed by split-flow MS detection.

$^1$H NMR spectra were recorded at 500.13 MHz on a Bruker Avance DRX500 instrument or at 250.13 MHz on a Bruker AC 250 instrument. Deuterated methylenchloride (99.8% D), chloroform (99.8% D) or dimethyl sulfoxide (99.8% D) were used as solvents. TMS was used as internal reference standard. Chemical shift values are expressed in ppm-values. The following abbreviations are used for multiplicity of NMR signals: s=singlet, d=doublet, t=triplet, q=quartet, qui=quintet, h=heptet, dd=double doublet, dt=double triplet, dq=double quartet, tt=triplet of triplets, m=multiplet and b=broad singlet.

For ion-exchange chromatography, the following material was used: SCX-columns (1 g) from Varian Mega Bond Elute, Chrompack cat. No. 220776. Prior to use, the SCX-columns were pre-conditioned with 10% solution of acetic acid in methanol (3 mL). For de-complexation by irradiation, a ultraviolet light source (300 W) from Philipps was used. As starting polymer supports for solid phase synthesis, Wang-resin (1.03 mmol/g, Rapp-Polymere, Tuebingen, Germany) was used.

Preparation of Intermediates $\eta^6$-1,2-Dichlorobenzene-$\eta^5$-cyclopentadienyliron(II) hexafluorophosphate Ferrocene (167 g), anhydrous aluminium trichloride (238 g) and powdered aluminium (24 g) were suspended in 1,2-dichlorobenzene (500 mL) and heated to 90° C. in a nitrogen atmosphere for 5 h with intensive stirring. The mixture was cooled to room temperature and water (1000 mL) was added carefully in small portions while cooling on an ice bath. Heptane (500 mL) and diethylether (500 mL) were added, and the mixture was stirred at room temperature for 30 minutes. The mixture was extracted with diethylether (3×300 mL). The aqueous phase was filtered, and aqueous ammonium hexafluorophosphate (60 g in 50 mL water) was added in small portions under stirring. The product was allowed to precipitate at room temperature. After 3 hours the precipitate was filtered off, washed intensively with water and dried in vacuo (50° C.) to give 81 g (21%) of the title compound as a light yellow powder. $^1$H NMR (D$_6$-DMSO): 5.29 (s, 5H); 6.48 (m, 2H); 7.07 (m, 2H).

Preparation of Polystyrene-Bound Amines

4-[(piperazin-1-yl)carbonyloxymethyl]phenoxymethyl polystyrene

4-[(4-Nitrophenoxy)carbonyloxymethyl]phenoxymethyl polystyrene (267 g, 235 mmol) was suspended in dry N,N-dimethylformamide (2 L). N-Methylmorpholine (238.0 g, 2.35 mol) and piperazine (102.0 g, 1.17 mol) were added and the mixture was stirred at room temperature for 16 h. The resin was filtered off and washed with N,N-dimethylformamide (2×1 L), tetrahydrofuran (2×1 L), water (1×500 mL), methanol (2×1 L), tetrahydrofuran (2×1 L) and methanol (1×1 L). Finally, the resin was washed with dichloromethane (3×500 mL) and dried in vacuo (25° C., 36 h) to yield an almost colourless resin (240.0 g).

The following polystyrene bound diamines were prepared analogously:

4-[(1,4-Diazepan-1-yl)carbonyloxymethyl]phenoxymethyl polystyrene

Preparation of resin-bound $\eta^6$-aryl-$\eta^5$-cyclopentadienyliron(II) hexafluorophosphates 4-({-4-[$\eta^6$-(2-Chlorophenyl)-$\eta^5$-cyclopentadienyliron(II)]piperazin-1-yl}carbonyloxymethyl)phenoxymethyl polystyrene hexafluorophosphate (Intermediate for 1a-1 h and 1k-1l)

4-[(piperazin-1-yl)carbonyloxymethyl]phenoxymethyl polystyrene (115.1 g, 92 mmol) was suspended in dry tetrahydrofuran (1.6 L), and $\eta^6$-1,2-dichlorobenzene-$\eta^5$-cyclopentadienyliron(II) hexafluorophosphate (76.0 g, 184 mmol) was added followed by potassium carbonate (50.9 g, 368 mmol). The reaction mixture was stirred at 60° C. for 16 h. After cooling to room temperature, the resin was filtered off and washed with tetrahydrofuran (2×500 mL), water (2×250 mL), tetrahydrofuran (2×500 mL), water (2×250 mL), methanol (2×250 mL), dichloromethane (2×250 mL) and methanol (2×250 mL). Finally, the resin was washed with dichloromethane (3×500 mL) and dried in vacuo (25° C., 36 h) to yield a dark orange resin (142 g).

The following polystyrene bound iron-complex was prepared analogously:

4-({4-[$\eta^6$-(2-Chloro-phenyl)-$\eta^5$-cyclopentadienyliron(II)]-[1,4]-diazepan-1-yl}carbonyloxymethyl)phenoxymethyl polystyrene hexafluorophosphate (Intermediate for 1i and 1j)

Preparation of Further Intermediates 1-tert-Butoxycarbonyl-4-[2-(4-methylphenylsulfanyl)phenyl]piperidin-4-ol A solution of BuLi (2.5 Min hexane, 12.0 ml, 30 mmol) was slowly added to a stirred solution of 1-bromo-2-(4-methylphenylsulfanyl)benzene (30 mmol) in dry THF (75 ml) under Argon at −78° C. The solution was stirred for 10 min before 4-oxo-piperidine-1-carboxylic acid tert-butyl ester (5.98 g, 30 mmol) was added in one portion. The solution was allowed to warm up to room temperature and then stirred for 3 h. Saturated aqueous NH$_4$Cl (150 ml) was added and the solution was extracted with ethylacetate (150 ml). The organic phase was washed with brine, dried (MgSO$_4$) and the solvent was evaporated in vacuo. Crude 1 was purified by flash chromatography on silica gel (eluent: Ethylacetat/heptane 20:80) to produce the target compound as a white foam. LC/MS (m/z) 399.3 (MH$^+$); RT=3.82; purity (UV, ELSD):

98%, 100%; yield: 5.02 g (42%). 1-tert-Butyloxycarbonyl-4-[2-(4-methylphenylsulfanyl)phenyl]-3,5-dioxopiperazine (Intermediate for 2a)

2-(4-Methylphenylsulfanyl)aniline (2.9 g, 13.5 mmol) was dissolved in dry THF (200 mL) and placed under a nitrogen atmosphere. N-(tert-butylocycarbonyl)iminodiacetic acid (4.7 g, 20.2 mmol) and carbonyl diimidazole (4.2 g, 40.4 mmol) were added to the solution and the reaction was refluxed for 60 hours. The reaction mixture was cooled to room temperature and ethyl acetate (500 mL) was added. The resulting solution was then washed with 2 N NaHCO$_3$ (2×200 mL), 2 N HCl (2×200 mL) and saturated sodium chloride solution (100 mL) and the solvents evaporated in vacuo. Yield 6.0 g, 107%, $^1$H NMR (CDCl$_3$) 1.5 (s, 9H); 2.32 (s, 3H); 4.4-4.6 (m, 4H); 7.02-7.18 (m, 3H); 7.2-7.45 (m, 5H).

The following 3,5 diketopiperazine derivatives were prepared in an analogous fashion:
1-tert-Butyloxycarbonyl-4-[2-(4-chlorophenylsulfanyl)phenyl]-3,5-dioxopiperazine (Intermediate for 2b)
1-tert-Butyloxycarbonyl-4-[2-(4-methoxyphenylsulfanyl)-4-chlorophenyl]-3,5-dioxopiperazine (Intermediate for 2c)
1-tert-Butyloxycarbonyl-4-[2-(4-methoxyphenylsulfanyl)-4-methylphenyl]-3,5-dioxopiperazine (Intermediate for 2d)
1-tert-Butyloxycarbonyl-4-[2-(4-methoxyphenylsulfanyl)-5-methylphenyl]-3,5-dioxopiperazine (Intermediate for 2e)
1-tert-Butyloxycarbonyl-4-[2-(4-fluorophenylsulfanyl)-5-methylphenyl]-3,5-dioxopiperazine (Intermediate for 2f)
1-tert-Butyloxycarbonyl-4-[2-(4-methoxyphenylsulfanyl)-5-trifluoromethylphenyl]-3,5-dioxopiperazine (Intermediate for 2 g)

2-(3-Methylpiperazin-1-yl)phenylamine (intermediate for 3a)

Fluoronitrobenzene (7.1 g, 50 mmol) was dissolved in DMF (100 mL) containing triethylamine (10 g, 100 mmol) and placed under a nitrogen atmosphere. To the solution was added 2-methyl-piperazine (5.5 g, 55 mmol). The reaction was heated to 80° C. for 16 hours. The reaction was allowed to cool to room temperature before the solvent was reduced to half volume in vacuo. Ethyl acetate (200 mL) and ice-water (250 mL) were added to the solution and the product was extracted with diethyether (2×200 mL). The aqueous phase was saturated with sodium chloride and extracted with ethyl acetate (2×200 mL). The organic phases were combined, washed with saturated brine, dried over magnesium sulfate, filtered and the filtrate was concentrated in vacuo. The product (10.5 g) was dissolved in ethanol (250 mL). Palladium on charcoal catalyst (10% w/w, 2.2 g) was added to the solution and the solution was hydrogenated in a Parr apparatus at 3 bar for 3 hours. The solution was filtered and the solvents evaporated in vacuo to give the aniline product. Yield (8.0 g, 83%)

The following intermediates were prepared in an analogous fashion:
2-(3,5-Dimethylpiperazin-1-yl)phenylamine (intermediate for 3b)

Compounds of the Invention

Example 1

1a, 1-[2-(2-Trifluoromethylphenylsulfanyl)phenyl]piperazine

To a solution of 2-trifluoromethylthiophenol (1.75 g, 9.8 mmol) in a 1:1 mixture of tetrahydrofuran/dimethylformamide (30 mL), sodium hydride (7.4 mmol, 60% in mineral oil) was carefully added at room temperature (Caution: Generation of hydrogen). The mixture was stirred for an additional 30 min after the generation of hydrogen had ceased. Subsequently, 4-({4-[η$^6$-(2-chloro-phenyl)-η$^5$-cyclopentadienyliron(II)]piperazin-1-yl}carbonyloxymethyl)phenoxymethyl polystyrene hexafluorophosphate (3.5 g, 2.45 mmol) was added and the mixture was stirred at 55° C. for 12 h. After cooling to room temperature, the resin was filtered off and washed with tetrahydrofuran (2×50 mL), tetrahydrofuran/water (1:1) (2×50 mL), N,N-dimethylformamide (2×50 mL), water (2×50 mL), methanol (3×50 mL), tetrahydrofuran (3×50 mL), and subsequently with methanol and tetrahydrofuran (each 50 mL, 5 cycles). Finally, the resin was washed with dichloromethane (3×50 mL) and dried in vacuo (25° C., 12 h) to yield a dark orange resin. The thus obtained resin and a 0.5 M solution of 1,10-phenanthroline in 3:1 mixture of pyridine/water (20 mL) was placed in light-transparent reactor tube. The suspension was agitated by rotation under irradiation with visible light for 12 h. The resin was filtered and washed with methanol (2×25 mL), water (2×25 mL) and tetrahydrofuran (3×25 mL) until the washing solutions were colourless (approx. 5 cycles) and the irradiation procedure was repeated until decomplexation was complete (approx. 5 cycles). After the decomplexation was completed, the resin was washed with dichlormethane (3×25 mL) and dried in vacuo (25° C., 12 h) to obtain a light brown resin. 100 mg (77 µmol) of the thus obtained resin were suspended in a 1:1 mixture of trifluoroacetic acid and dichlormethane (2 mL) and stirred at room temperature for 2 h. The resin was filtered off and washed with methanol (1×0.5 mL) and dichloromethane (1×0.5 mL). The filtrates were collected and the volatile solvents evaporated in vacuo. The crude product was purified by preparative LC-MS and subsequently by ion-exchange chromatography. LC/MS (m/z) 339 (MH$^+$); RT=2.39; purity (UV, ELSD): 92%, 100%; overall yield: 1 mg (4%).

The following arylpiperazines and aryl[1,4]diazepanes were prepared analogously:
1b, 1-[2-(4-Bromophenylsulfanyl)phenyl]piperazine: LC/MS (m/z) 350 (MH$^+$); RT=2.46; purity (UV, ELSD): 75%, 92%; yield: 2 mg (7%).
1c, 1-{2-[4-(Methylsulfanyl)phenylsulfanyl]phenyl}piperazine: LC/MS (m/z) 317 (MH$^+$); RT=2.39; purity (UV, ELSD): 91%, 100%; yield: 2 mg (8%).
1d, 1-[2-(4-Hydroxyphenylsulfanyl]phenyl}piperazine: LC/MS (m/z) 287 (MH$^+$); RT=1.83; purity (UV, ELSD): 84%, 100%; yield: 3 mg (13%).
1e, 1-[2-(2,4-Dimethylphenylsulfanyl)phenyl]piperazine: LC/MS (m/z) 299 (MH$^+$); RT=2.48; purity (UV, ELSD): 95%, 100%; yield: 4 mg (17%).
1f, 1-[2-(3,5-Dimethylphenylsulfanyl)phenyl]piperazine: LC/MS (m/z) 299 (MH$^+$); RT=2.51; purity (UV, ELSD): 96%, 100%; yield: 5 mg (21%).
1g, 1-[2-(2,6-Dimethylphenylsulfanyl)phenyl]piperazine: LC/MS (m/z) 299 (MH$^+$); RT=2.42; purity (UV, ELSD): 97%, 100%; yield: 4 mg (17%).
1h, 1-[2-(2,5-Dimethylphenylsulfanyl)phenyl]piperazine: LC/MS (m/z) 299 (MH$^+$); RT=2.46; purity (UV, ELSD): 97%, 100%; yield: 1 mg (4%).
1i, 1-[2-(2-Trifluoromethylphenylsulfany)phenyl]-[1,4]-diazepane: LC/MS (m/z) 353 (MH$^+$); RT=2.46; purity (UV, ELSD): 70%, 96%; yield: 1 mg (4%).
1j, 1-[2-(3-Methylphenylsulfanyl)phenyl]-[1,4]-diazepane: LC/MS (m/z) 299 (MO; RT=2.44; purity (UV, ELSD): 76%, 93%; yield: 1 mg (4%).

1k, 1-[2-(4-Butylphenoxy)phenyl]piperazine: LC/MS (m/z) 311 (MH$^+$); RT=2.77; purity (UV, ELSD): 91%, 100%; yield: 4 mg (17%).

1l, 1-[2-(4-Methoxyphenoxy)phenyl]piperazine: LC/MS (m/z) 285 (MH$^+$); RT=2.08; purity (UV, ELSD): 93%, 100%; yield: 4 mg (18%)

Example 2

2a, 2-(4-Methylphenylsulfanyl)phenyl-1-piperazine hydrochloride 1-tert-Butyloxycarbonyl-4-[2-(4-methylphenylsulfanyl) phenyl]-3,5-dioxo-piperazine (5.5 g, 13 mmol) was dissolved in dry THF (50 mL) and placed under a nitrogen atmosphere. Borane tetrahydrofuran complex (50 mmol, 1.0 M) in tetrahydrofuran was added and the reaction was refluxed for ten minutes. Excess borane was quenched by the addition of an excess of ethyl acetate and the reaction was refluxed for a further 20 minutes. The reaction was allowed to cool to room temperature before hydrogen chloride dissolved in methanol (50 mL, 4 M) was added and the reaction was refluxed for 4.5 hours. The reaction was allowed to cool to room temperature and the reaction was concentrated in vacuo. The compound was crystallised from the gum residue by the addition of ether/methanol solution. The crystalline solid was filtered and washed with ether/methanol (1:1) to give a white crystalline solid. Yield (2.0 g, 47%) $^1$H NMR (D$_6$-DMSO) 2.35 (s, 3H); 3.18 (br s, 8H); 6.68 (d, 2H); 7.02 (m, 1H); 7.18 (m, 1H); 7.3-7.5 (m, 4H); MS (MH$^+$) 285.

The following compounds were prepared in an analogous fashion:

2b, 1-[2-(4-chlorophenylsulfanyl)phenyl]piperazine LC-MS (m/z) 305.1 (MH$^+$) RT=2.46 purity (UV, ELSD) 71%, 91% yield 0.096 g, 100%

2c, 1-[2-(4-methoxyphenylsulfanyl)-4-chlorophenyl]piperazine LC-MS (m/z) (MH$^+$) 335.2 RT=2.38 purity (UV, ELSD) 98%, 100% yield 0.22 g, 62%

2d, 1-[2-(4-methoxyphenylsulfanyl)-4-methylphenyl]piperazine LC-MS (m/z) (MH$^+$) 315.1 RT=2.33 purity (UV, ELSD) 97%, 100% yield 0.21 g, 56%

2e, 1-[2-(4-methoxyphenylsulfanyl)-5-methylphenyl]piperazine LC-MS (m/z) (MH$^+$) 315.2 RT=2.38 (UV, ELSD)$_{98}$%, 100% yield 2.3 g, 58%

2f, 1-[2-(4-fluorophenylsulfanyl)-5-methylphenyl]piperazine LC-MS (m/z) (MH$^+$) 303.2 RT=2.46 (UV) 98% yield 2.1 g, 62%

2g, 1-[2-(4-Methoxyphenylsulfanyl)-5-trifluoromethylphenyl]piperazine LC-MS (m/z) (MH$^+$) 369 RT=2.50 (UV, ELSD) 96%, 100% yield 0.54 g, 31%

Example 3

3a, 1-[2-(4-Chlorophenylsulfanyl)phenyl]-3-methylpiperazine 2-(3-Methylpiperazin-1-yl)phenylamine (0.96 g, 5 mmol) was dissolved in 30 mL water containing sulfuric acid (0.28 mL, 5.2 mmol) and the solution was cooled to 0° C. and sodium nitrite (0.36 g, 5.2 mmol) was added. The reaction was stirred for 30 minutes before the pH of the reaction was adjusted to pH 7 with sodium acetate. The diazonium salt solution was then added dropwise to a solution of 4-chlorothiophenol in a suspension of copper (0.3 g, 5 mmol) in 2 M NaOH (4 mL). After addition, the reaction mixture was heated to 60° C. for 30 minutes before being allowed to cool to room temperature and ethyl acetate (10 mL) was added. The reaction mixture was filtered and the layers were separated. The aqueous layer was extracted with ethyl acetate (2×10 mL). The combined organic phases were dried (MgSO$_4$) and volatile solvents evaporated in vacuo. The crude product was purified by flash chromatography using silica gel, eluting with ethyl acetate/methanol/ammonia 96:3:1. The pure product was isolated as a colourless oil. Yield (0.18 g, 11%) 1H NMR (CDCl$_3$, 500 MHz) 1.12 (d, 3H); 2.6-2.72 (br m, 2H); 3.0-3.15 (m, 5H); 6.9 (m, 2H); 7.08 (d, 1H); 7.15 (m, 1H); 7.25-7.35 (m, 4H); MS (MH$^+$) 319.1.

The following compound was prepared in an analogous fashion:

3b, 1-[2-(4-Chlorophenylsulfanyl)phenyl]-3,5-dimethylpiperazine LC-MS (m/z) (MH)+333.1 RT=2.29 (UV, ELSD) 83%, 100% yield 0.54 g, 31%.

Example 4

4a, 4-[2-(4-Methylphenylsulfanyl)phenyl]-3,6-dihydro-2H-pyridine

Concentrated aq hydrochloric acid (10 ml) was added to a stirred solution of 1-tert-butoxycarbonyl-4-[2-(4-methylphenylsulfanyl)phenyl]piperidin-4-ol (0.84 g, 2.1 mmol) in acetic acid (30 mL). The solution was boiled under reflux overnight, cooled to room temperature and then stirred in an ice bath. An aqueous solution of NaOH (9.1 M, 40 mL) was slowly added and the unclear solution was extracted with ethyl acetate (2×40 ml). The combined organic phases were dried (MgSO$_4$) and the solvents evaporated in vacuo. The crude material (0.48 g) was dissolved in ethyl acetate (3.2 mL) at 50° C. and a solution of oxalic acid (0.11 g) in EtOH (3.2 mL) was slowly added. The target compound was collected as a white oxalic salt. $^1$H (DMSO-d$_6$) δ 7.3-7.2 (m, 7H); 7.15 (m, 1H); 7.00 (m, 1H); 5.6 (d, 1H); 3.7 (d, 2H); 3.25 (t, 2H); 2.6 (m, 2H); 2.3 (s, 3H). LC/MS (m/z) 282.2 (MH$^+$); RT=2.24; purity (UV, ELSD): 99%, 100%; yield: 0.31 g (40%).

The following derivative was prepared analogously:

4b, 4-[2-(4-Methoxyphenylsulfanyl)phenyl]-3,6-dihydro-2H-pyridine

LC/MS (m/z) 298 (MH$^+$); RT=2.00; purity (UV, ELSD): 97%, 100%; yield: 0.28 g (30%).

Example 5

5a, 4-[2-(4-Methylphenylsulfanyl)phenyl]piperidine

Methyl Chloro-oxo-acetate (1.37 g, 11.25 mmol) was added to a stirred solution of 1-tert-butoxycarbonyl-4-[2-(4-methylphenylsulfanyl)phenyl]piperidin-4-ol (3.00 g, 7.5 mmol) and 4-(dimethylamino)pyridine (1.65 g, 13.5 mmol) in a mixture of dry CH$_3$CN (24 ml) and CHCl$_3$ (12 mL) at 0° C. under argon. The reaction mixture was allowed to reach room temperature and then stirred 2 h. Ethyl acetate (140 mL) was added and some salts were removed by filtration through celite. The organic phase was washed with sat. NaHCO$_3$ (140 ml), brine (140 mL) and dried (MgSO$_4$). The solvents were evaporated in vacuo and the crude material was dried in vacuo. This material was dissolved in dry toluen (48 mL) under argon. Bu$_3$SnH (3.27 g, 11.25 mmol) and AIBN (0.31 g, 1.88 mmol) were added. The solution was stirred under argon at 90° C. for 2.5 h. The solvent was evaporated in vacuo, and the crude material was purified by flash chromatography on silicagel (eluent: a stepwise gradient of ethylacetat in heptane from 10:90 to 20:80) to produce 44244-methylphenylsulfanyl)phenyl)-piperidine-1-carboxylic acid tert-butyl ester as a clear oil (1.94 g, 67%). This oil was dissolved in MeOH (9.2 mL) and HCl in diethylether (2.0 M) was added at 0° C. The reaction mixture was allowed to warm to room temperature and stirred overnight. The target compound was collected as its hydrochloride. M.p 229-231° C. Calculated for $C_{18}H_{21}NS \cdot HCl$: C, 67.58; H, 6.63; N, 4.38. Found: C, 67.33; H, 6.97; N, 4.31. LC/MS (m/z) 284 (MH$^+$); RT=2.12; purity (UV, ELSD): 96%, 100%; yield: 0.26 g (46%).

Inhibition of the Uptake of [$^3$H]Serotonin into Whole Rat Brain Synaptosomes

The compounds were tested with respect to their 5-HT reuptake inhibiting effect by measuring their ability to inhibit the uptake of [$^3$H]serotonin into whole rat brain synaptosomes in vitro. The assay was performed as described by Hyttel *Psychopharmacology* 1978, 60, 13.

5-HT$_{2C}$ Receptor Efficacy as Determined by Fluorometry

The compounds were tested with respect to their efficacy on 5-HT$_{2C}$ receptor-expressing CHO cells (Euroscreen) as determined by fluorometric imaging plate reader (FLIPR) analysis. This assay was carried out according to Molecular Devices Inc. instructions for their FLIPR Calcium Assay Kit and as modified from Porter et al. *British Journal of Pharmacology* 1999, 128, 13.

Preferred compounds of the present invention exhibit serotonin reuptake inhibition below 200 nM (IC$_{50}$) in the assay above. More preferred are the compounds which exhibit inhibition below 100 nM and most preferably below 50 nM. Compounds of particular interest exhibit serotonin reuptake inhibition below 10 nM;

The invention claimed is:

1. A compound represented by the formula I wherein
Y represents C or CH;
X represents O or S;
m is 2;
p is 0, 1, 2, 3, 4, 5, 6, 7 or 8;
q is 0, 1, 2, 3 or 4;
s is 0, 1, 2, 3, 4 or 5;
the dotted line represents an optional bond;
each R$^1$ is independently selected from the group represented by C$_{1-6}$-alkyl, or two R$^1$ attached to the same carbon atom may form a 3-6-membered spiro-attached cycloalkyl;
each R$^2$ is independently selected from the groups represented by halogen, cyano, nitro, C$_{1-6}$-alk(en/yn)yl, C$_{1-6}$-alk(en/yn)yloxy, C$_{1-6}$-alk(en/yn)ylsulfanyl, hydroxy, hydroxy-C$_{1-6}$-alk(en/yn)yl, halo-C$_{1-6}$-alk(en/yn)yl, halo-C$_{1-6}$-alk(en/yn)yloxy, C$_{3-8}$-cycloalk(en)yl, C$_{3-8}$-cycloalk(en)yl-C$_{1-6}$-alk(en/yn)yl, acyl, C$_{1-6}$-alk(en/yn)yloxycarbonyl, C$_{1-6}$-alk(en/yn)ylsulfonyl, or —NR$^x$R$^y$; —NR$^x$CO—C$_{1-6}$-alk(en/yn)yl;

each R$^3$ is independently selected from a group represented by halogen, cyano, nitro, C$_{1-6}$-alk(en/yn)yl, C$_{1-6}$-alk(en/yn)yloxy, C$_{1-6}$-alk(en/yn)ylsulfanyl, hydroxy, hydroxy-C$_{1-6}$-alk(en/yn)yl, halo-C$_{1-6}$-alk(en/yn)yl, halo-C$_{1-6}$-alk(en/yn)yloxy, C$_{3-8}$-cycloalk(en)yl, C$_{3-8}$-cycloalk(en)yl-C$_{1-6}$-alk(en/yn)yl, C$_{1-6}$-alk(en/yn)ylsulfonyl, aryl, C$_{1-6}$-alk(en/yn)yloxycarbonyl, acyl, —NR$^x$CO—C$_{1-6}$-alk(en/yn)yl, —CONR$^x$R$^y$ or NR$^x$R$^y$;

or two adjacent R$^3$ substituents together form a heterocycle fused to the phenyl ring selected from the group consisting of wherein W is O or S, and R' and R" are hydrogen or C$_{1-6}$-alkyl:

or two adjacent R$^3$ substituents together form a fused heteroaromatic system containing one, two or three heteroatoms, wherein each R$^x$ and R$^y$ is independently selected from the group represented by hydrogen, C$_{1-6}$-alk(en/yn)yl, C$_{3-8}$-cycloalk(en)yl, C$_{3-8}$-cycloalk(en)yl-C$_{1-6}$alk(en/yn)yl, or aryl; or R$^x$ and R$^y$ together with the nitrogen to which they are attached form a 3-7-membered ring which optionally contains one further heteroatom;

or a pharmaceutically acceptable acid addition salt thereof.

2. The compound according to claim 1, wherein p is 0, 1 or 2.

3. The compound according to claim 1, wherein R$^1$ is C$_{1-6}$-alkyl.

4. The compound according to claim 1, wherein q is 0, 1 or 2.

5. The compound according to claim 1, wherein R$^2$ is trifluoromethyl, or C$_{1-6}$-alkyl.

6. The compound according to claim 1, wherein s is 1 or 2.

7. The compound according to claim 1, wherein R$^3$ is selected from the group consisting of halogen, C$_{1-6}$-alkoxy, C$_{1-6}$-alkylsulfanyl, C$_{1-6}$-alkyl, hydroxy or trifluoromethyl.

8. A pharmaceutical composition comprising a compound according to claim 1 or a pharmaceutically acceptable acid addition salt thereof and at least one pharmaceutically acceptable carrier or diluent.

9. A method for the treatment of an affective disorder in a living animal body, comprising administering a therapeutically effective amount of a compound according to claim 1 or a pharmaceutically acceptable acid addition salt thereof.

10. The method of claim 9, wherein the living animal body is a human.

11. The method of claim 9, wherein the affective disorder is selected from the group consisting of depression, anxiety disorder, and obsessive compulsive disorder.

12. The method of claim 11, wherein the anxiety disorder is selected from the group consisting of general anxiety disorder and panic disorder.

* * * * *